(12) United States Patent
Burns et al.

(10) Patent No.: US 6,332,091 B1
(45) Date of Patent: Dec. 18, 2001

(54) DIAGNOSIS OF EDEMA

(75) Inventors: David Hugh Burns; Lorenzo Leonardi, both of Montreal; Luis Oppenheimer, Winnipeg, all of (CA)

(73) Assignees: McGill University, Montreal; University of Manitoba, Winnipeg, both of (CA)

( * ) Notice: Subject to any disclaimer, the term of this patent is extended or adjusted under 35 U.S.C. 154(b) by 0 days.

(21) Appl. No.: 09/484,244

(22) Filed: Jan. 18, 2000

Related U.S. Application Data

(63) Continuation of application No. PCT/CA98/00688, filed on Jul. 16, 1998.

(30) Foreign Application Priority Data

Jul. 18, 1997 (CA) .................................................. 2210791

(51) Int. Cl.[7] .................................................... A61B 6/00
(52) U.S. Cl. ........................................................ 600/475
(58) Field of Search .................................... 600/310, 407, 600/473, 475, 476, 477; 356/432, 433

(56) References Cited

U.S. PATENT DOCUMENTS

| | | | | |
|---|---|---|---|---|
| 4,874,949 | * | 10/1989 | Harris et al. | 250/343 |
| 5,601,080 | * | 2/1997 | Oppenheimer | 128/633 |
| 5,645,061 | * | 7/1997 | Kessler et al. | 128/634 |
| 5,916,152 | * | 6/1999 | Oppenheimer et al. | 600/310 |

FOREIGN PATENT DOCUMENTS

| | | |
|---|---|---|
| 44 10 888 | 5/1995 | (DE) . |
| 0 575 712 | 12/1993 | (EP) . |
| WO 96/04535 | 2/1996 | (WO) . |

* cited by examiner

*Primary Examiner*—Marvin M. Lateef
*Assistant Examiner*—Eleni Mantis Mercader
(74) *Attorney, Agent, or Firm*—Swabey Ogilvy Renault

(57) ABSTRACT

Pulmonary edema in the lung is detected by exposing a lung under investigation to infrared radiation, especially near-infrared radiation; measuring the reflected radiation scattered by the lung as a spectral response to the presence of water in the lung; comparing the reflected radiation with calibrated values and evaluating occurrence of pulmonary edema from the comparison.

11 Claims, 16 Drawing Sheets

DIAGNOSIS OF EDEMA

CROSS REFERENCE TO RELATED APPLICATIONS

This application is a continuation of PCT/CA98/00688 filed Jul. 16, 1998, in which the United States of America was designated and elected, and which remains pending in the International Phase until Jan. 18, 2000, which application in turn claims priority from Canadian Patent Application S.N. 2,210,791 filed Jul. 18, 1997.

TECHNICAL FIELD

This invention relates to a method and apparatus for detecting pulmonary edema.

BACKGROUND ART

Pulmonary edema is an abnormal accumulation of fluid in the extravascular tissue and spaces of the lung which results in poor respiration.

Pulmonary edema represents a common problem seen in many clinical settings, and there are a number of causes of pulmonary edema such as an increase in hydrostatic pressure, increase in capillary permeability and a decrease in lymphatic clearance (Ref. 1).

The increase in hydrostatic pressure is caused by an increase in the venous pressure which usually occurs due to heart failure. The change in the permeability of the capillaries is also an important cause of pulmonary edema. If the exchange between plasma and tissue is altered in such a manner as to allow the exchange of fluid between the interstitial space and plasma more readily, then this results in an increase in fluid. The third possible cause of pulmonary edema is the decrease in lymphatic clearance. In the case where this is altered there will be an accumulation of fluid in the interstitial space. The two distinct consequences of the fluid increase are, 1) the alveoli volume will decrease in size due to the volume increase of the interstitial space and 2) a reduction in the alveoli space due to fluid accumulation.

Pulmonary edema is readily detectable by conventional chest radiographs, the present standard being X-ray. Attempts have been made to use X-rays as both a qualitative and quantitative assessment of edema (Ref. 2). The method can be performed in one of two ways, a visual inspection or a Computed Tomography (CT) of the radiograph. There are a number of small features which can be seen on plain chest radiographs. The most common is a scattered increase in lung radiographic density sometimes referred to as "clouding" (Ref. 3). This change is often difficult to recognize. CT scans involve a densitometric analysis of the radiograph (Refs. 4 and 6). However, this approach to quantitative pulmonary edema is limited. The problem with the diagnosis of pulmonary edema is the interpretation of the radiographs. The methods involve observing the physiological changes experienced pre- and post-pulmonary edema. The changes involved are increases in vessel diameters, bronchial wall thickening, and opacities associated with fluid accumulation. In the extreme case of pulmonary edema, a dense spot on the radiograph as well as physiological enlargement of the chest cavity make the identification simple. In the early stages of edema, radiographs can be misleading and interpreted in a number of manners making detection virtually impossible. Magnetic Resonance Imaging (MRI) and Positron Emission Tomography (PET) are also used but experience the same problem of identification (Ref. 5).

While chest radiographs are an invaluable asset to the qualitative identification of edema, they are of limited value in diagnosis of pulmonary edema in early stages of its development. Pulmonary edema is life-threatening and difficult to treat; existing radiographic methods for its diagnosis only provide effective diagnosis at an advanced stage of development.

DISCLOSURE OF THE INVENTION

It would be highly advantageous to have other methods for detecting pulmonary edema, especially methods capable of providing a diagnosis of pulmonary edema at an early stage of its development.

In accordance with one aspect of the invention, there is provided a method of detecting pulmonary edema in a lung comprising:
a) exposing a lung under investigation to infrared radiation,
b) measuring reflected infrared radiation scattered by the lung as a spectral response to the presence of water in the lung,
c) comparing the reflected radiation with calibrated values of reflected radiation for lung water levels indicative of pulmonary edema, and
d) evaluating occurrence of pulmonary edema in the lung from the comparison developed in step c).

In accordance with another aspect of the invention there is provided an apparatus for detecting pulmonary edema in a lung comprising:
i) a plurality of optical fibers effective to transmit infrared radiation from a source to a lung under investigation and to transmit reflected scattered radiation from said lung,
ii) a source of infrared radiation operatively associated with said fibers for transmission of infrared radiation,
iii) detector means for receiving reflected scattered radiation from said fibers, and issuing signals responsive thereto,
iv) evaluating means for receiving said signals and comparing the received signals with calibrated values.

In accordance with another aspect of the invention there is provided use of infrared radiation to detect pulmonary edema in a lung.

DESCRIPTION OF PREFERRED EMBODIMENTS OF THE INVENTION

The invention provides an alternative non-invasive method in the detection of pulmonary edema employing infrared spectroscopy especially near-infrared spectroscopy. The Near-Infrared (NIR) region is composed of wavelengths from 700–2500 nm. The spectral region between 600–1300 nm provides a therapeutic window having special significance in biomedical applications. The main absorptions in this region are due to components which contain C—H, O—H, and N—H vibrations. When tissue becomes irradiated with light in this region, some of the light is absorbed by the tissue while a large portion of the light is diffusely scattered. Most of the interactions of light with tissue are scattering events and such events are highly forward scattering, i.e. light propagates in a forward direction. The combined attributes of the low absorption and the highly forward scattering nature of tissue allows for a substantial penetration and a high remittance of the scattered light whereby the near infrared is suitable for studying biological and physiological characteristics such as changed levels of water as exhibited in pulmonary edema.

In preferred embodiments the infrared radiation has a wavelength between 600 and 1300 nm.

In the method, the lung is typically exposed in step a) to the radiation at a plurality of sites of the lung, and step b) comprises measuring the reflected radiation scattered by this plurality of sites.

MODES FOR CARRYING OUT THE INVENTION

EXAMPLES

Experimental

Figure 1:
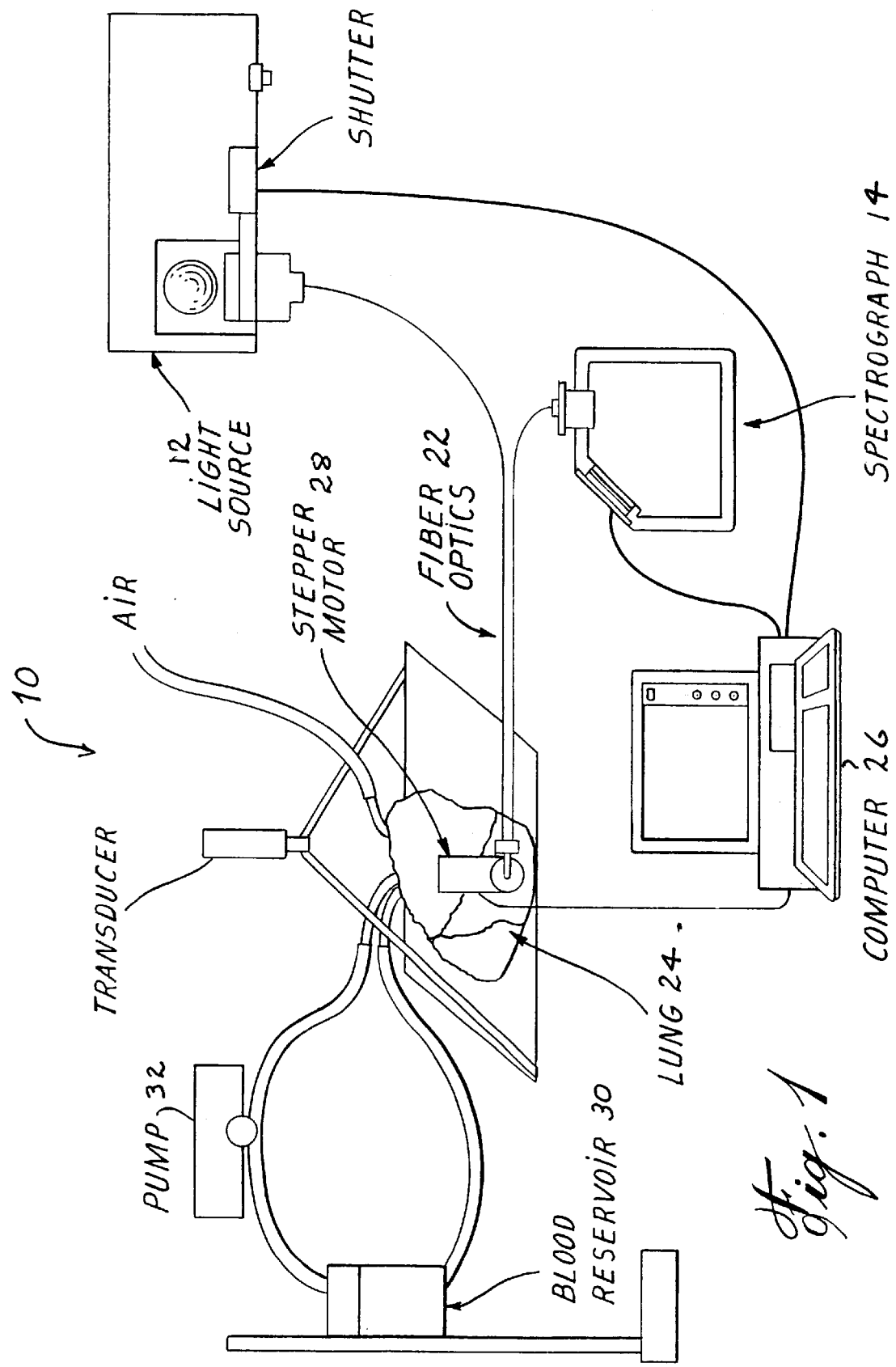
FIG. 1 illustrates an experimental assembly for evaluating a lung employing the methodology of the invention.
Figure 2:
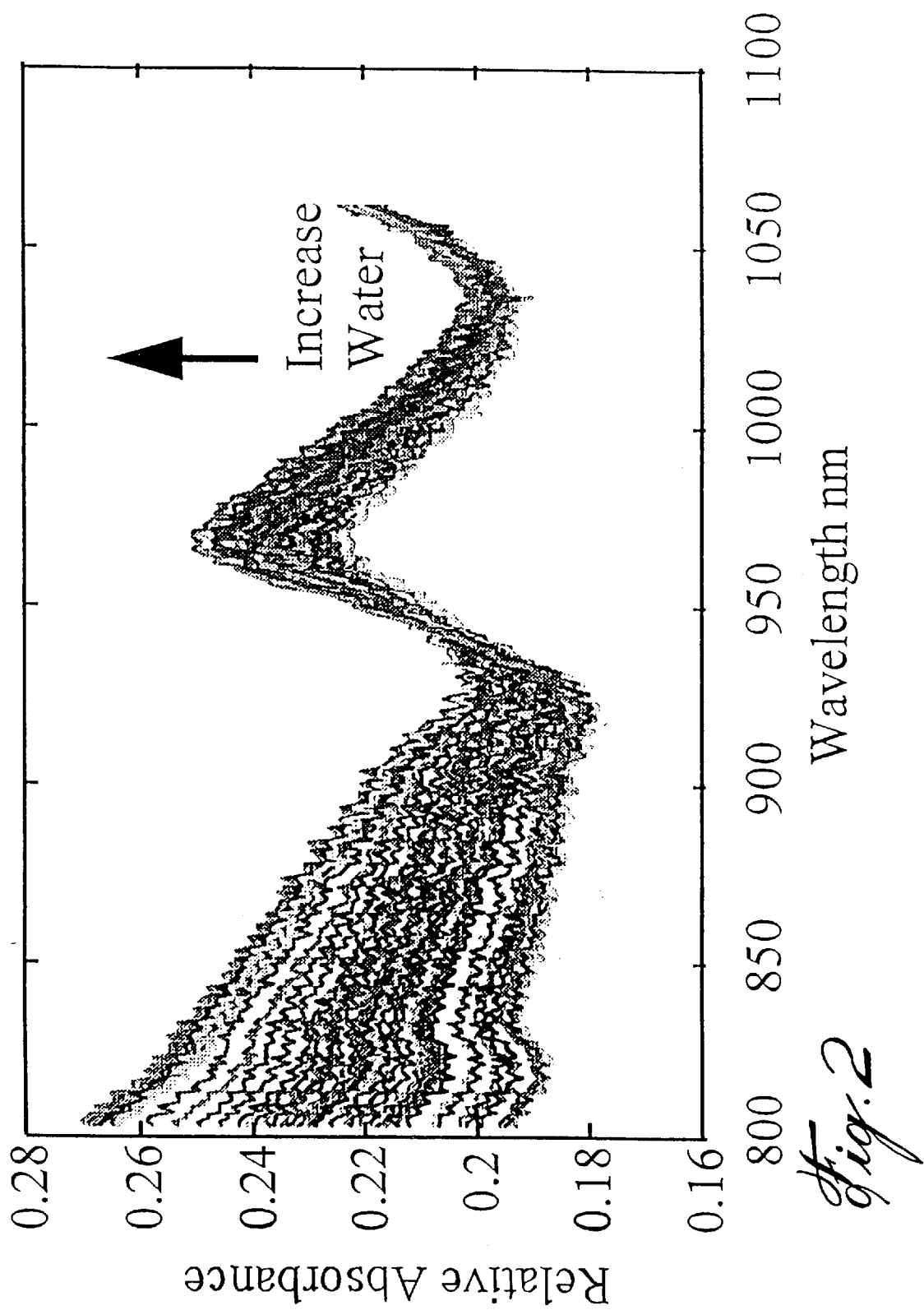
FIG. 2 shows how the spectra changes with increase in water.
Figure 3A:
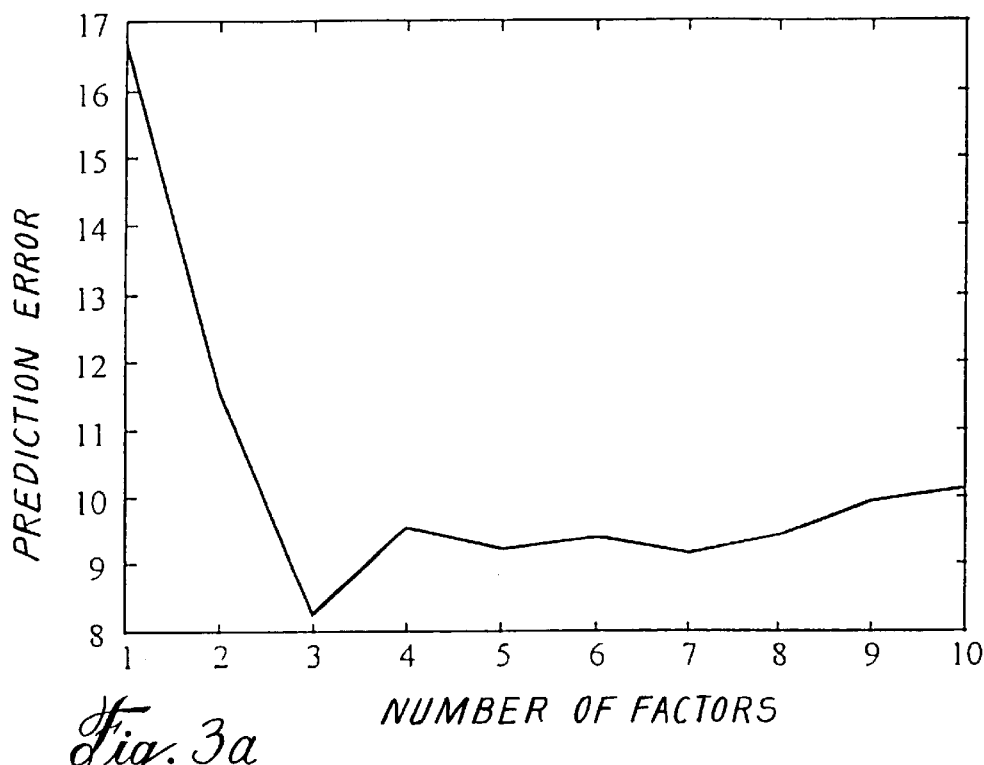
FIG. 3a is a plot of prediction error (PRESS) and the number of factors.
Figure 3B:
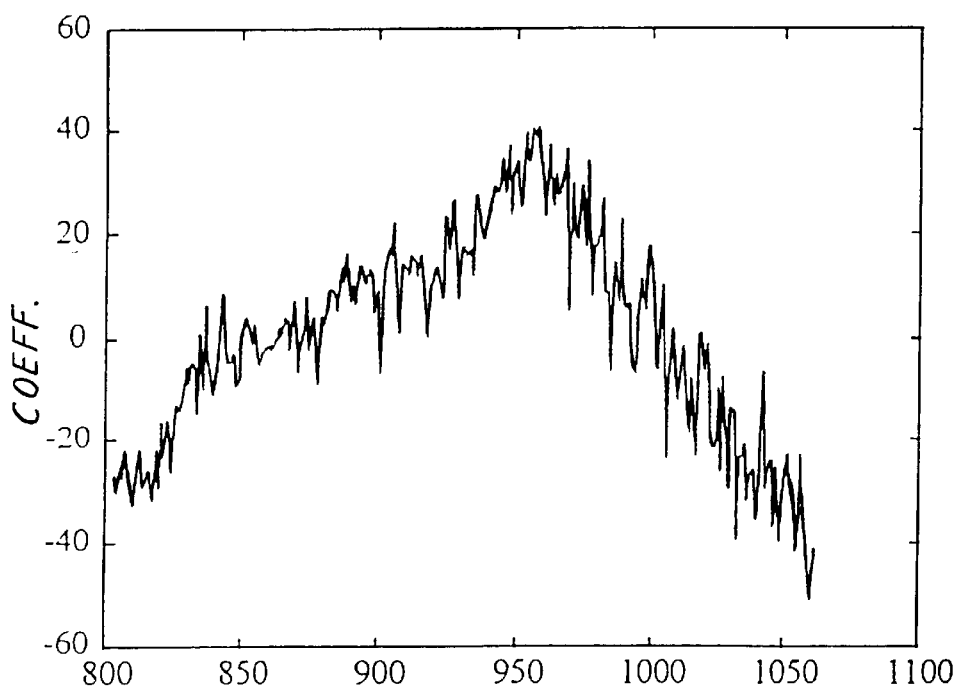
FIG. 3b is a plot of calibration coefficient and wavelength.
Figure 4A:
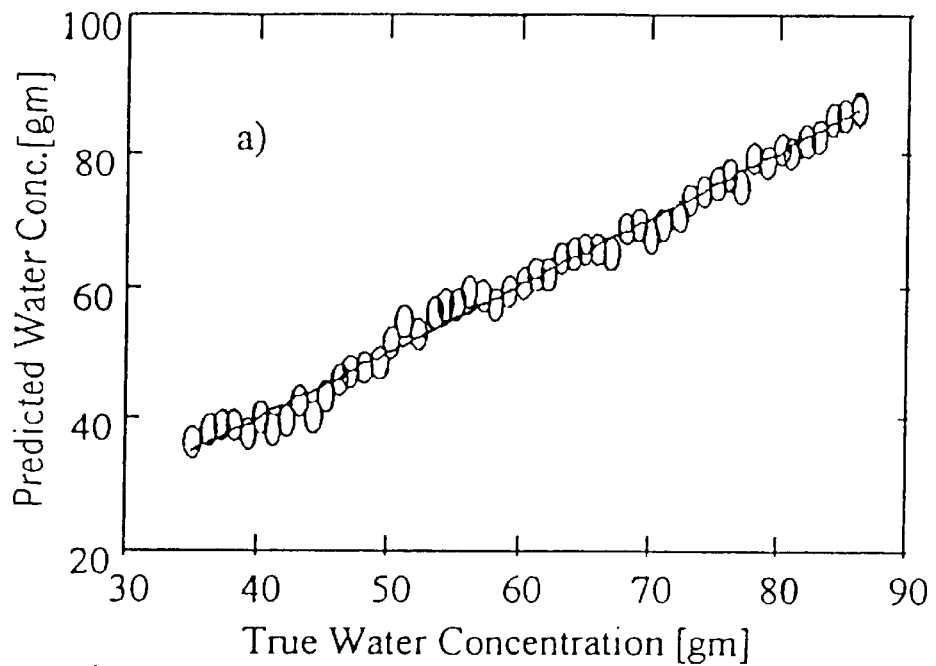
FIGS. 4a and 4b are plots for estimation of the absolute water content.
Figure 4B:
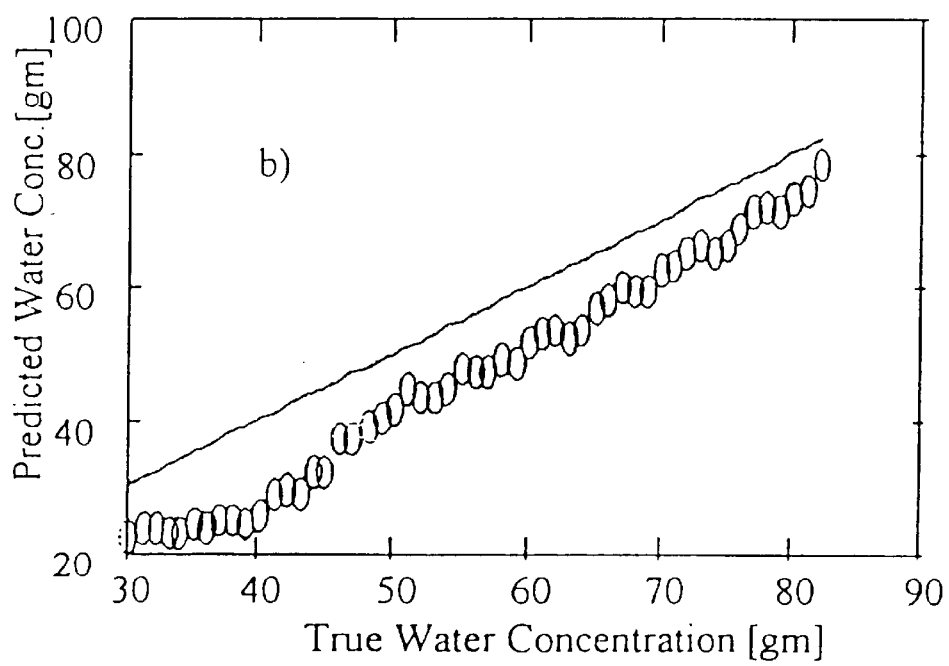
Figure 5A:
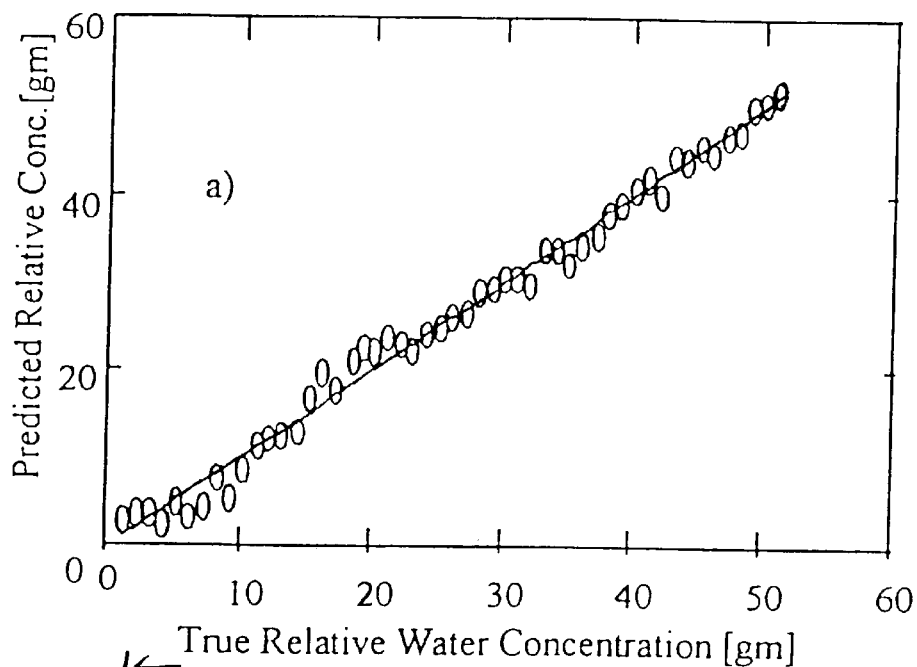
FIGS. 5a and 5b are plots for estimating relative change in water content.
Figure 5B:
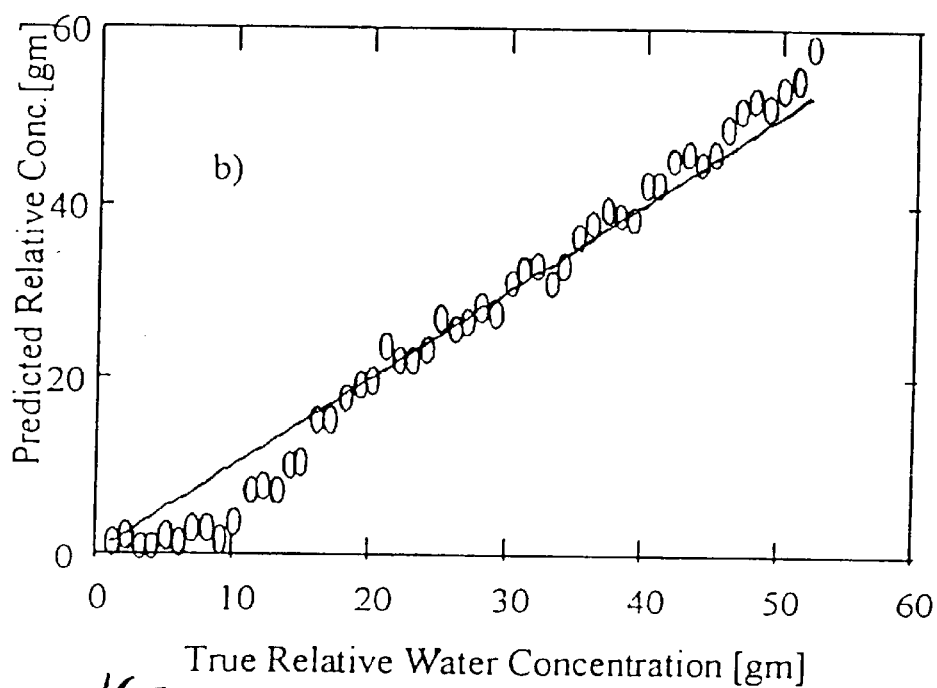
Figure 6:
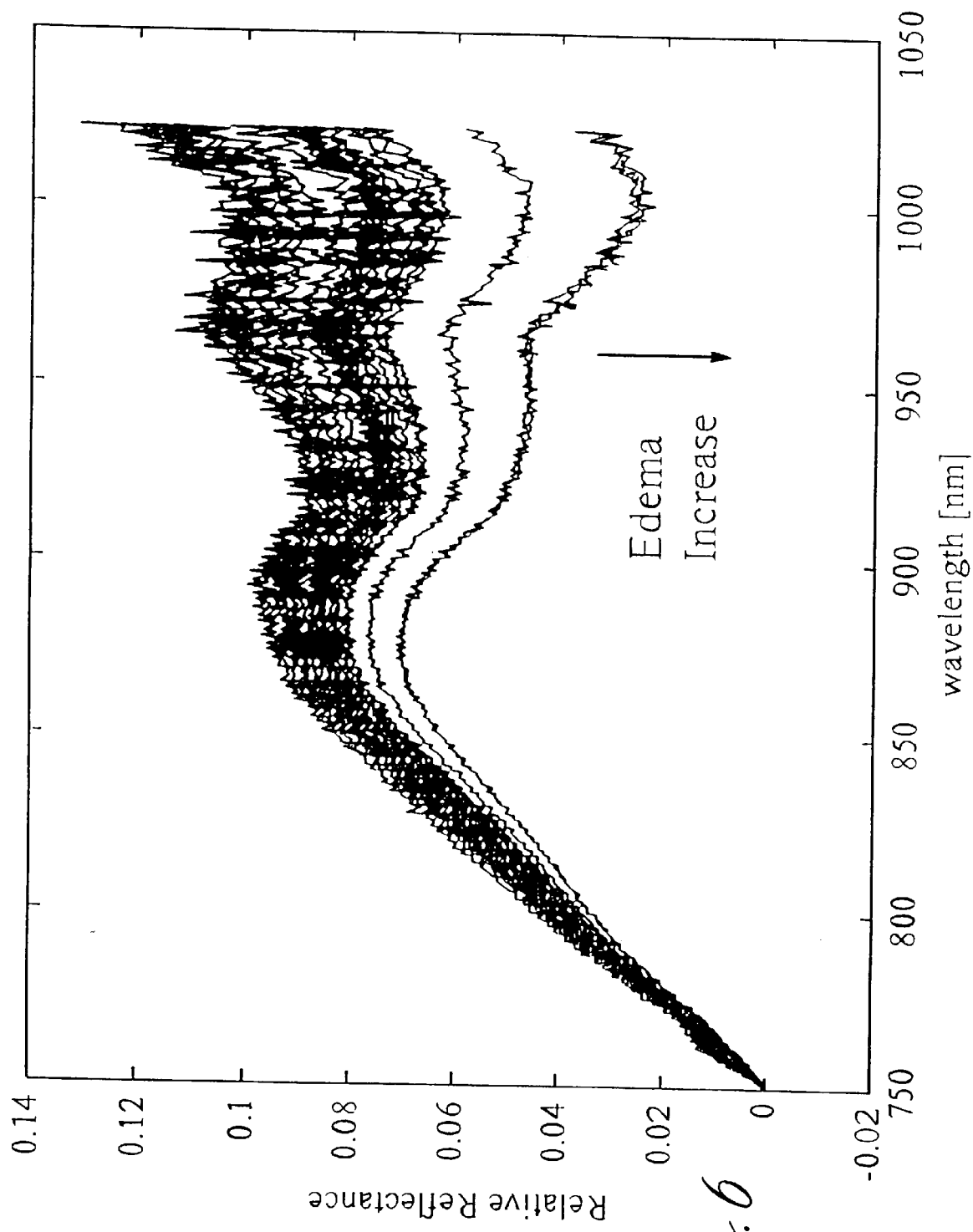
FIG. 6 is a plot demonstrating the change in spectral response with increase in edema.
Figure 7:
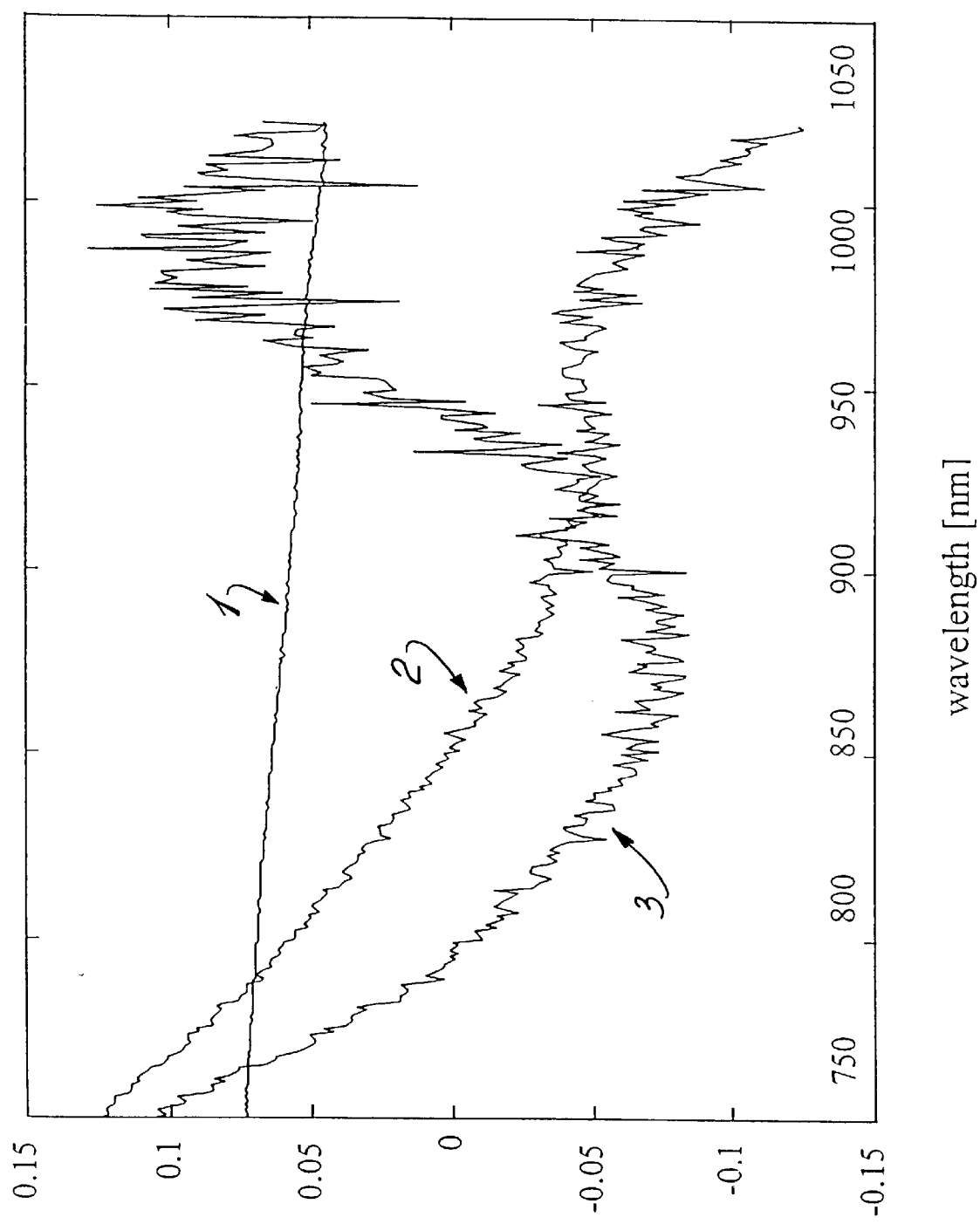
FIG. 7 is a plot illustrating the contribution of different factors to changes in the spectra with edema.
Figure 8:
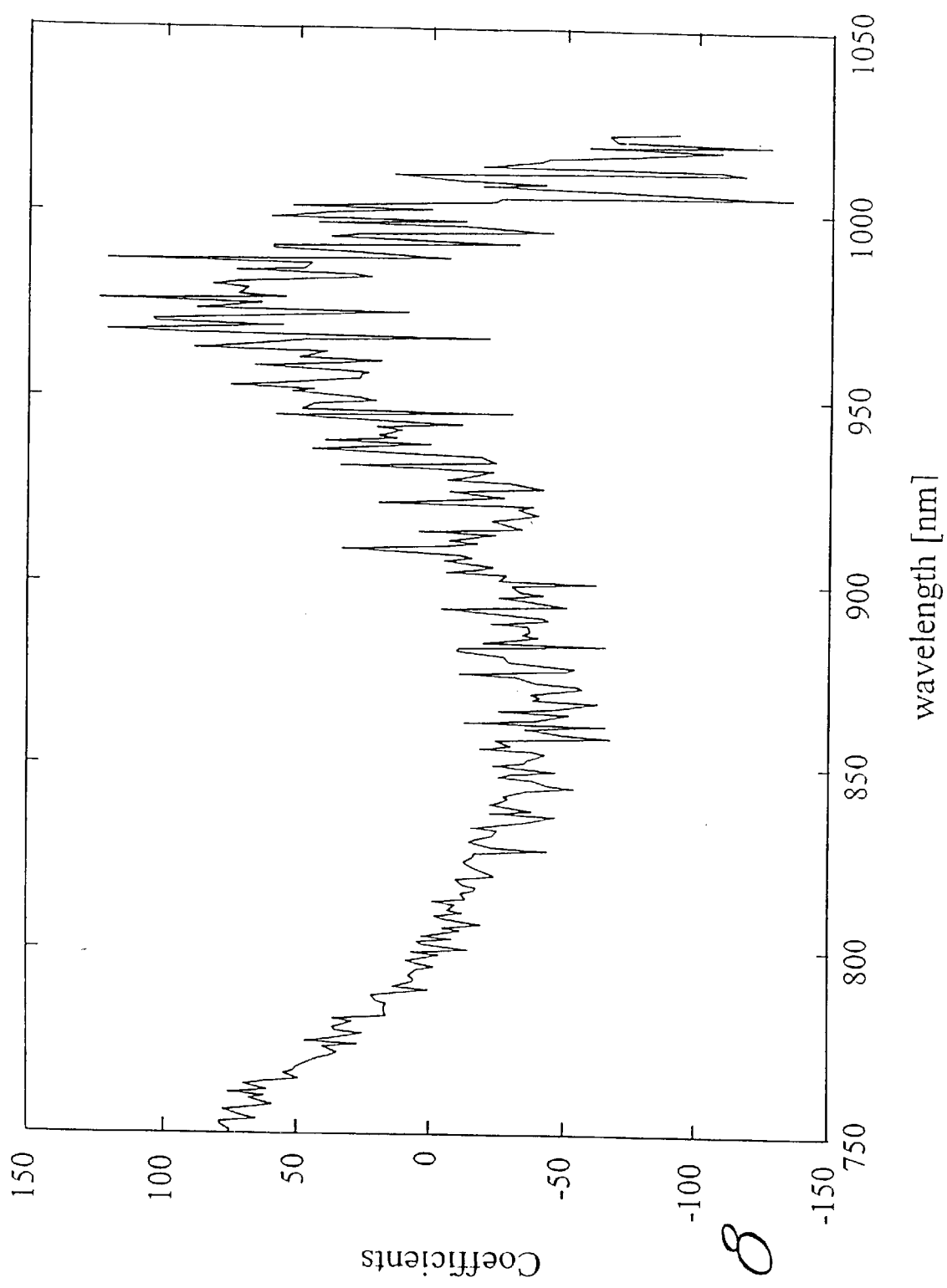
FIG. 8 is a plot of calibration coefficient with wavelength.

The setup 10 illustrated in FIG. 1 consisted of three main components: a light source 12, diode array spectragraph 14, and data acquisition board 16. The light source was a variable 150 watt tungsten halogen lamp covering the range from 320 to 2500 nm. The source is current regulated to provide better stability for long term use. Long exposure to intense light locally heats the sample, therefore the source was modified to incorporate a shutter 18. The shutter 18 was driven by a solenoid which was connected to a computer controlled relay 20.

Optics are used to collimate the light from the fiber optics 22 in the illumination and collection from the tissue. Both the optics and fibers 22 were mounted on a radial shaft connected to a computer controlled stepper motor 28. Different locations on the lung 29 can be sampled by rotation of the fibers 22 about the motor 28. The positioning system was compact (<7.5 cm dia.×5 cm) and provided a reliable means of moving the fiber optics 22 from one location to another. The collection fiber was attached to a diode array spectragraph 14 (American Holographics). The spectragraph contains a holographic diffraction grating capable of detecting light from 450 to 1050 nm. The detector is a 512 linear diode array (Hamamatsu Corp.) with a pixel size of 2.5 mm×25 $\mu$m. The diode array driver is computer controlled via a data acquisition board(National Instruments). The data acquisition board is a 16-bit 100 KHz board with multiple I/O signals. All software used in the collection from the spectragraph was written in C (Microsoft). The software collects and stores the data in a file and is then processed using routines written in Matlab (MathWorks).

1) Lung Phantom

To demonstrate the principles of an edemic response, a phantom was used to simulate the fluid accumulation. The phantom consisted of a reddish sponge approximately 50 cm×50 cm×30 cm in size with a mean pore size of 400 $\mu$m. The phantom was set on a balance to measure accurately the weight increase with the addition of water. Fiber optic probes were placed between the phantom and the dish to illuminate and collect the light to obtain spectral responses with accumulation of water. The sponge was slightly moistened to avoid sudden swelling when water comes into contact with it. The reference for the incident light was a 20 mm thick stack of white filter paper (Whatman 1). This assumes the reflected light from the filter paper mimics light scattered from the tissue with no absorber present. The collected spectra, with their corresponding change in water weight were introduced into the PLS regression.

2) In Vitro Experiment

The in vitro trials were made at the Health Sciences Center Hospital in Winnipeg, Manitoba. The dogs were anesthetized and prepared for the removal of the lobes. One of the two lobes was removed and set on a wired balance connected to a force transducer. The other lobe was also removed, inflated and frozen in liquid nitrogen for later use as a control in the morphometric analysis. During the removal of the first lobe, the dogs were desanguinated and the blood collected in a reservoir 30.

A reciprocating pump 32 connected to the reservoir was used to pump blood to and from the lung. The measurements were done at atmospheric pressure with a positive pressure of 10 mm water (98 pascals) placed in the lung airway.

Edema was induced in the lung by elevating the reservoir above the level of the lung thus increasing the venous pressure. The edemic response produced an increase in the weight of the lung measured by a force transducer. A PC-XT connected to a data acquisition board was used to digitize the change in weight from the force transducer. A similar setup to that employed in the phantom was used in the excised lung to measure the change in spectral response with edema seen in FIG. 1.

The fiber optic probes were placed 3 cm from the top of the lung illuminating a 28 $cm^2$ area. A transient response was induced by changing the hydrostatic pressure in the lung to separate the intervascular and extravascular components in the lung. The transient was produced by moving the blood reservoir to a higher level relative to the lung to increase the pressure. Spectra were collected before and during the transient response. During each of the cycles, spectra from two locations on the lobe were collected. The illuminated region was marked with India ink to identify the region for correlations with morphometric analysis. The lobes were frozen in liquid nitrogen transported to the Pathology Department at McGill for morphometric analysis.

The morphologic measurements of the lobes were made at McGill University in the Department of Pathology. Each lobe was graded semiquantitatively by light microscopy for interstitial and alveolar edema. Interstitial edema was graded on a scale from 0 to 3 (0 representing no edema and 3 the greatest amount of interstitial edema). Alveolar flooding was graded by estimating the percentage of alveolar surface area occupied by edema (0% representing no edema and 100% complete alveolar flooding). To validate the reproducibility of this technique, the slides were read independently by two observers, after which a consensus percentage of alveolar edema and interstitial edema was obtained and the results tabulated in Table 1.

FIG. (1) In Vitro lung setup.

The lobe was placed on a wire balance connected to a force transducer to measure the weight increase with edema. Fiber optic probes attached to a stepper motor are used to irradiate/collect the light. A computer controlled spectragraph disperses the light into the corresponding spectra.

Partial Least Squares Analysis

Partial Least Squares Regression (PLSR) is a multivariate method used in complex systems (Ref. 13). PLSR is a representation of the data whereby the complex spectra are reduced to their most predominate factors. The method consists of reducing a set of variables and using the compressed variables as an estimate. The compressed values will contain the main features of the data with the noise reduced. The relationship of the individual change in water concentrations to the spectra can be described in matrix notation as:

$$C = SB^t$$ Error! Switch argument not specified.

where C (n×1) represents the change in water concentration of n samples, S(n×m) the individual spectra of n samples with m wavelengths, and $B^t$ (m×1) the vector of calibration coefficients. From known values of C and S the calibration coefficients, $B^t$, can be estimated using the predominate factors from C and S. The calibration coefficients consist of the optimal number of factors used to estimate a prediction set. To determine the optimal number of factors, a means of Cross-Validation of the calibration set is given by the Predicted Error Sum of the Squares (PRESS). Typically, a plot of the number of factors and the PRESS shows a minima in the error. This minima corresponds to the minimal number of factors needed to describe a given set of calibration data with respect to an independent set of data. A calibration is constructed based on the optimal number of factors. The calibration consists of a series of coefficients which when multiplied by their corresponding wavelength and then summed provides the estimated values. A Standard Error is calculated as the mean variation between the true and estimated values as a means of comparison.

3) Lung Phantom

The PLSR model requires two sets of data, one for the construction of the calibration and another for the estimation. A series of spectra with their corresponding increase in water are displayed in FIG. (2). The data was processed using the PLS analysis to estimate the water content of the sponge.

FIG. (2) Phantom spectral response with change in water weight.

A plot of the PRESS vs the number of factors describe the relative predictive error in the model. Based on the PRESS, FIG. (3a), the minimal number of factors needed to describe the data are 3 with a predicted error of 8.18 gm. The calibration coefficients consist of the contributions of the 3 most predominate factors and is given by FIG. (3b). The coefficients have positive contributions in the 960 nm region i.e. water region. This corresponds to an increase in the water absorbance with increase in water. However, there is a negative correlation in the C-H region. The increase in water decreases amount of C-H in the sponge relative to the water.

FIG. (3)a) A PRESS plot.

The minimum number of factors required to estimate the water weight was 3. This is due to the three fundamental changes, namely, the change in OH, CH, and scattering with water b) Calibration coefficients. These are the coefficients used in the estimate of the water weight. This consists of performing a multiplication and summation of the coefficient with its corresponding spectra.

The calibration coefficients consisting of 3 factors were constructed and used to estimate the absolute water content, FIG. (4). The solid line in the figure is the "line of identity" and represents the ideal case. The slope and intercept were used as figures of merit on the ability of the calibration to estimate a given set of data. The adequacy of the calibration to follow the general edema trend can be seen in the slope. The intercept can be used to determine the systematic errors or offsets involved. Correlation coefficients are used as a means of validating the overall estimates by assigning a value to the fit. The relative standard error estimate provided a numeric error value associated with estimate. The plot of FIG. (4a) represents the estimate of the data used in the construction of calibration. The correlation coefficient for the estimation was 0.9952 with a standard error of 1.5095 gm. The slope and intercept of the line are 0.9902 and 0.2556 which are close to the ideal case. The estimation using an independent set of data, FIG. (4b), is another means of validation. The correlation coefficient for the estimate was 0.9900 with a standard error of 1.8166 gm. The slope and intercept of the line are 1.0714 and −9.8326. The slope is close to the ideal but the intercept seems to be off. This offset is due to the difference in the initial water content of the sponge making an absolute estimate of water weight difficult. Since the slope was close to the ideal case, this would suggest that a general trend is being followed. Instead of attempting an absolute water weight, an estimate of the relative change was made and seen in FIG. (5). The estimate of the calibration data is represented in FIG. (5a). The correlation coefficient for the estimate was 0.9948 with a standard error of 1.5386 gm. The slope and intercept of the line are 1.0002 and 0.0929 which are in good agreement with the ideal case. The estimate of the independent data set had a correlation coefficient of 0.9945 and standard error of 1.8460 gm. The slope and intercept of the line are 1.0578 and −1.6116, respectively.

FIG. (4) Absolute water weight.
  a) Estimation of the calibration set b) Estimation of an independent set.

FIG. (5) Change in water weight.
  a) estimation of the calibration set b) estimation of an independent set.

4) In Vitro Lung

The phantom has shown that the accumulation of water can be estimated using the NIR spectral responses. The changes in spectral response with increase in edema were observed and are depicted in FIG. (6). The data has been corrected at the 750 nm line. Since the lung has a different composition than the phantom, a spectral difference was expected.

FIG. (6) Lung spectral response with increase in edema.

The spectra have been corrected at the 750 nm line to reduce some of the non-linearties.

FIG. (7) In Vitro lung Weight Set.

The first and second contributions describe the sloping features to the spectra. This corresponds to the change in scattering with edema. The third contribution contains information on the change in C-H with water seen at 860 nm. The fourth describes the change in the O-H with edema or water increase.

The Weight Set, FIG. (7), represents linear combinations of the pure components in the spectra. The PLS analysis places the weights in order of importance starting with the predominate contribution. The first and second weights represented by 1 and 2 in FIG. (7), demonstrates an approximate linear relationship with wavelength. This was probably due to the changes in scattering as edema increased. The lung undergoes some structural changes as water increases. The lung began to swell since more of the space became occupied with water. This swelling changed the relative amount of water as well as the amount of scatter present. The third weight, 3, is a combination of the increase in water, decrease in the relative C-H and a decrease in the scattering. The lung is composed of many substances such as proteins, fats, collagen, etc. which are also present in the third weight set.

The optimal number of factors required to describe the data by the PRESS plot was 4 with estimated error 2.466. F-tests were performed based on the PRESS in choosing the optimal number of factors. The set of calibration coefficients based on the 4 most predominate factors is given in FIG. (8). The coefficients have a slightly positive correlation at 960 nm which is due to the water. The positive contribution of the C-H change is seen in the 860–900 nm region. The change in scattering is estimated by the coefficients by weighing more of the positive contributions at 860 nm and less at 960 nm i.e. an uneven distribution of water and C-H contributions.

Figure 9A:
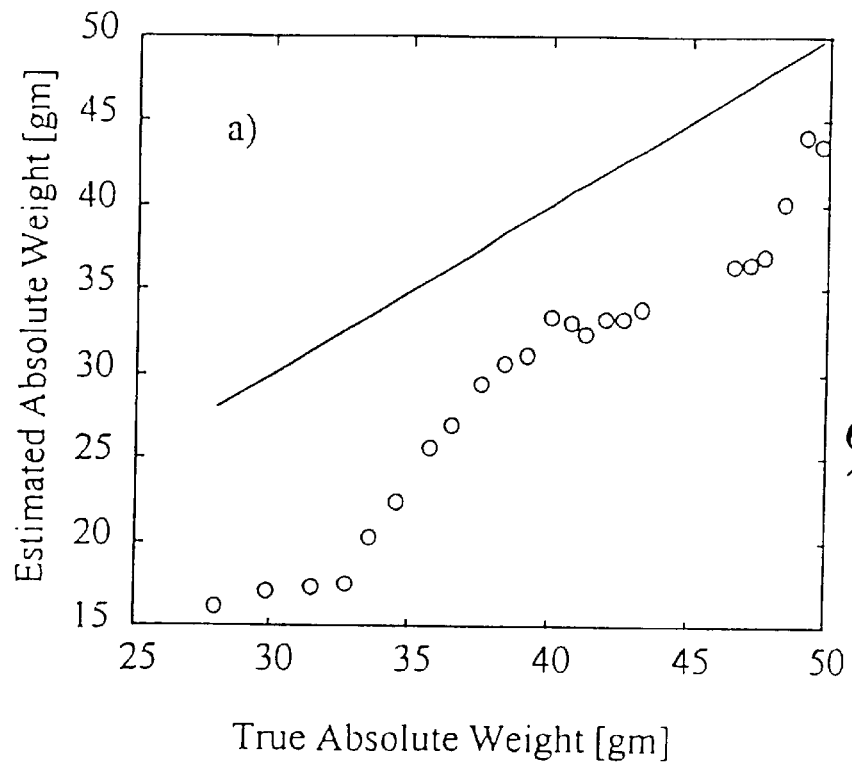
FIG. 9a is a plot showing an absolute measure of edema.
Figure 9B:
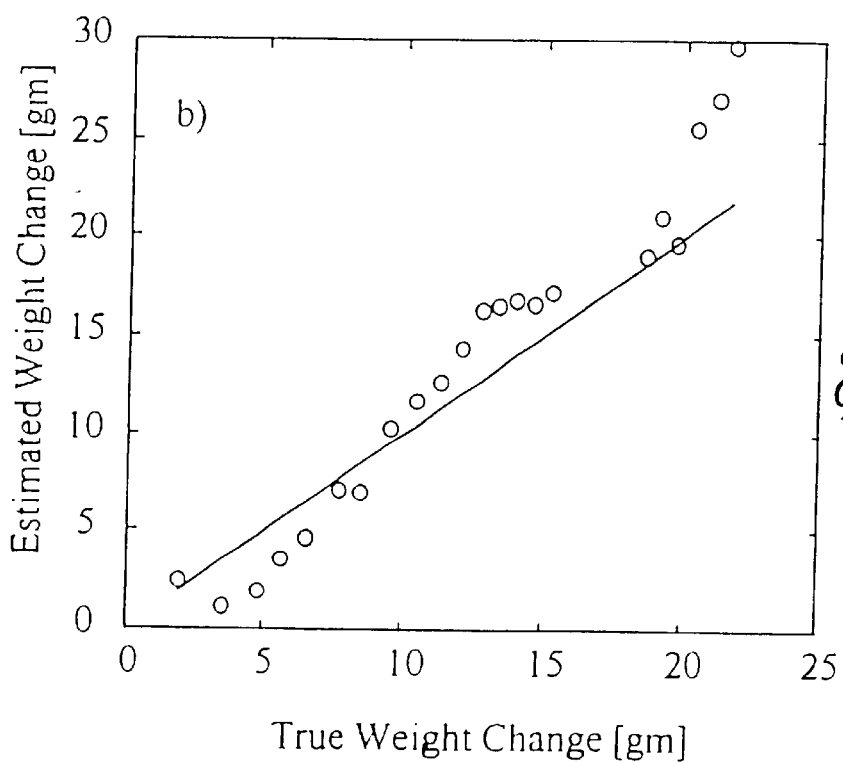
FIG. 9b is a plot showing change in edema.
Figure 10:
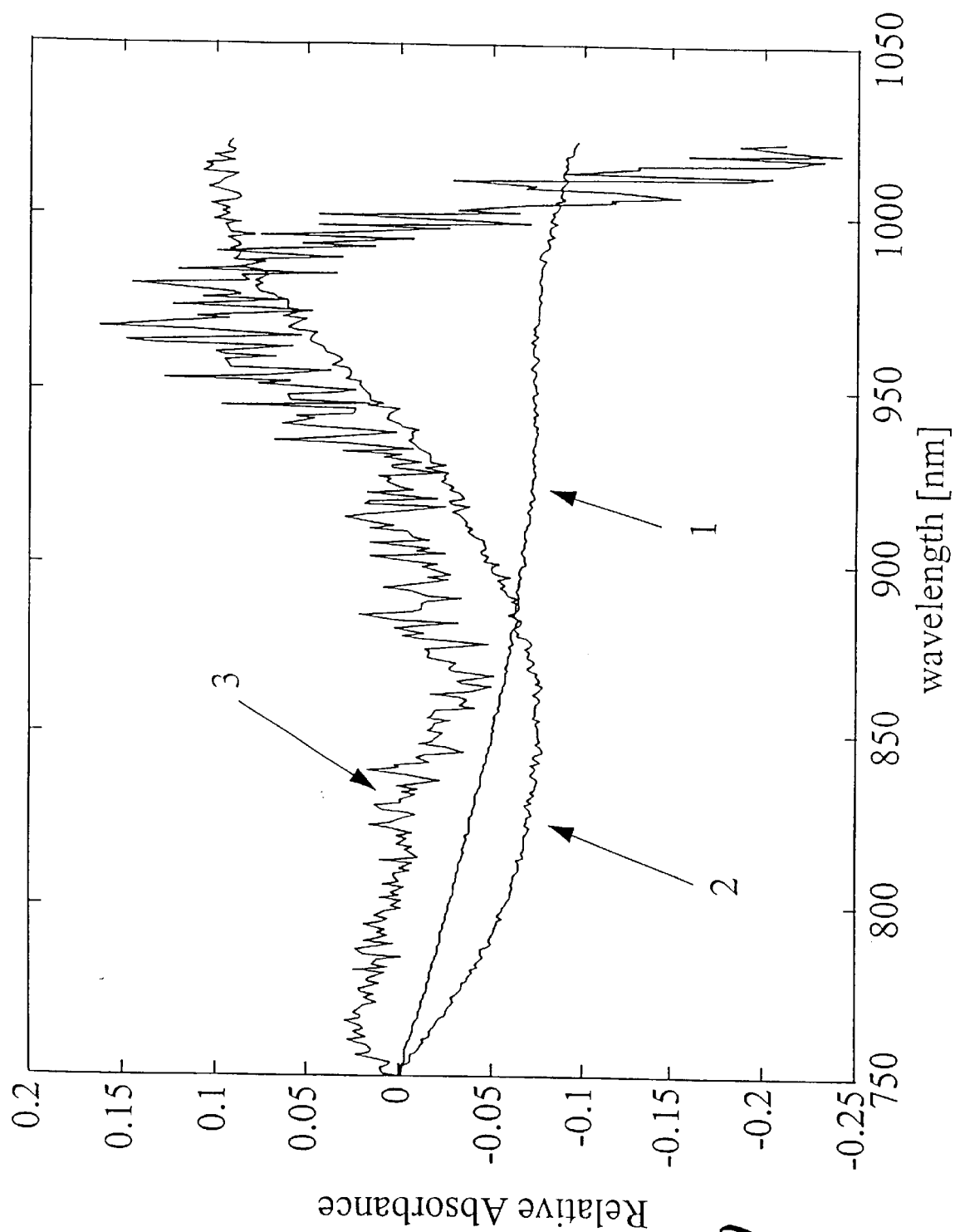
FIG. 10 is a plot illustrating the weight set from a PLS regression for different components of the spectra for edema.
Figure 11A:
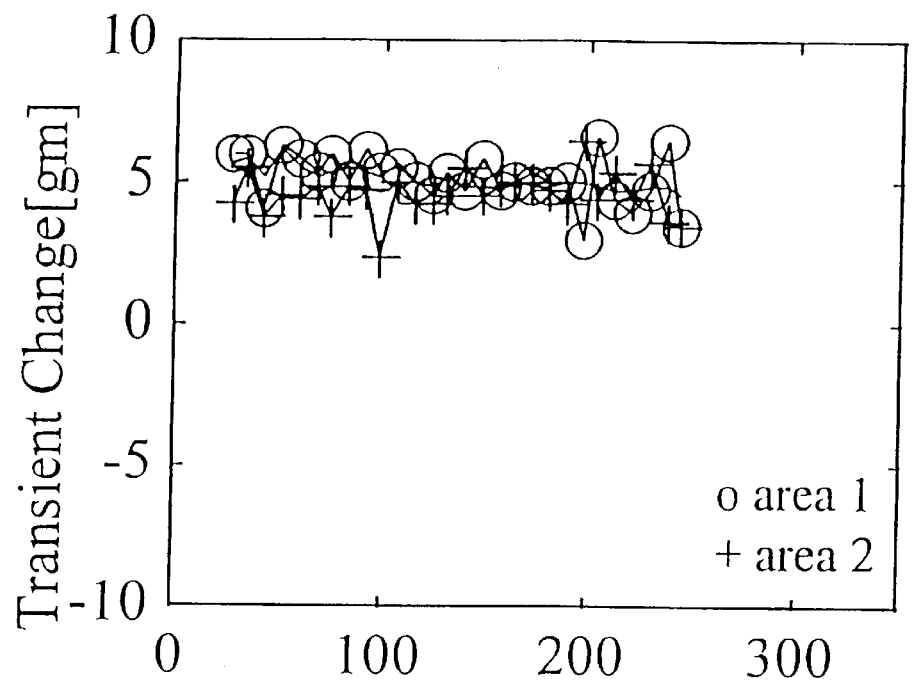
FIGS. 11A, 11B, 11C and 11D are plots of transient weight changes of a lung with time.
Figure 11B:
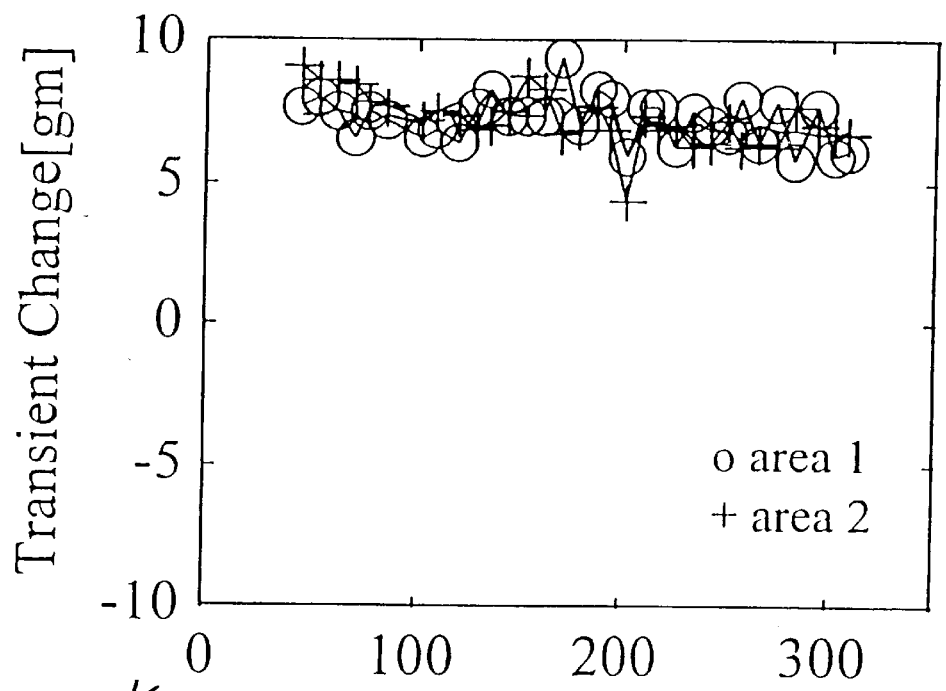
Figure 11C:
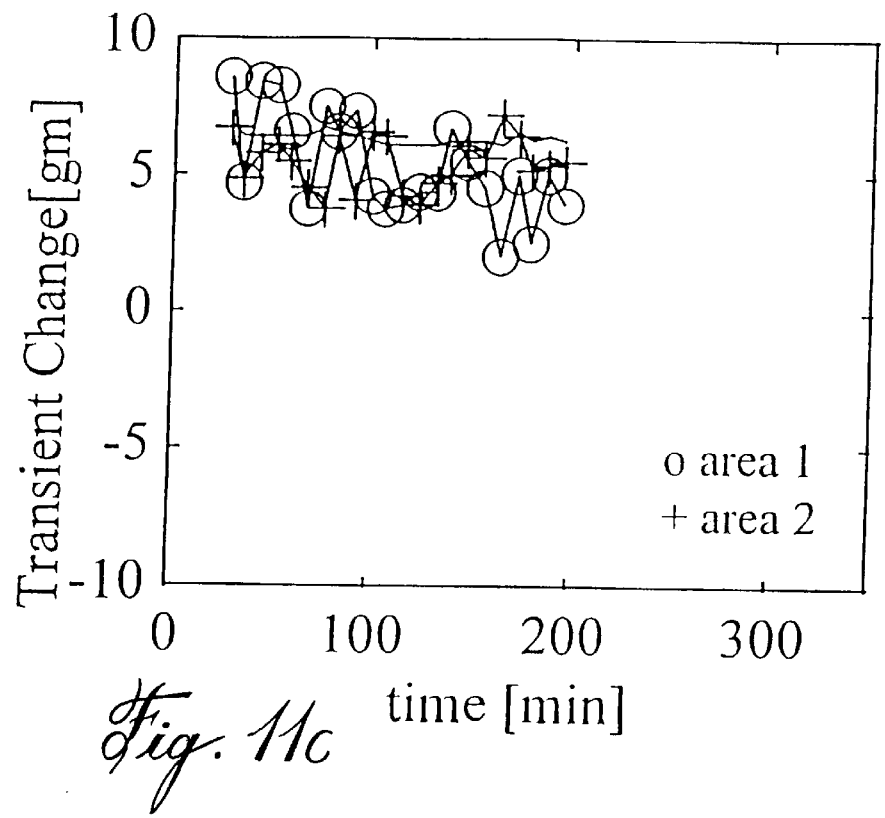
Figure 11D:
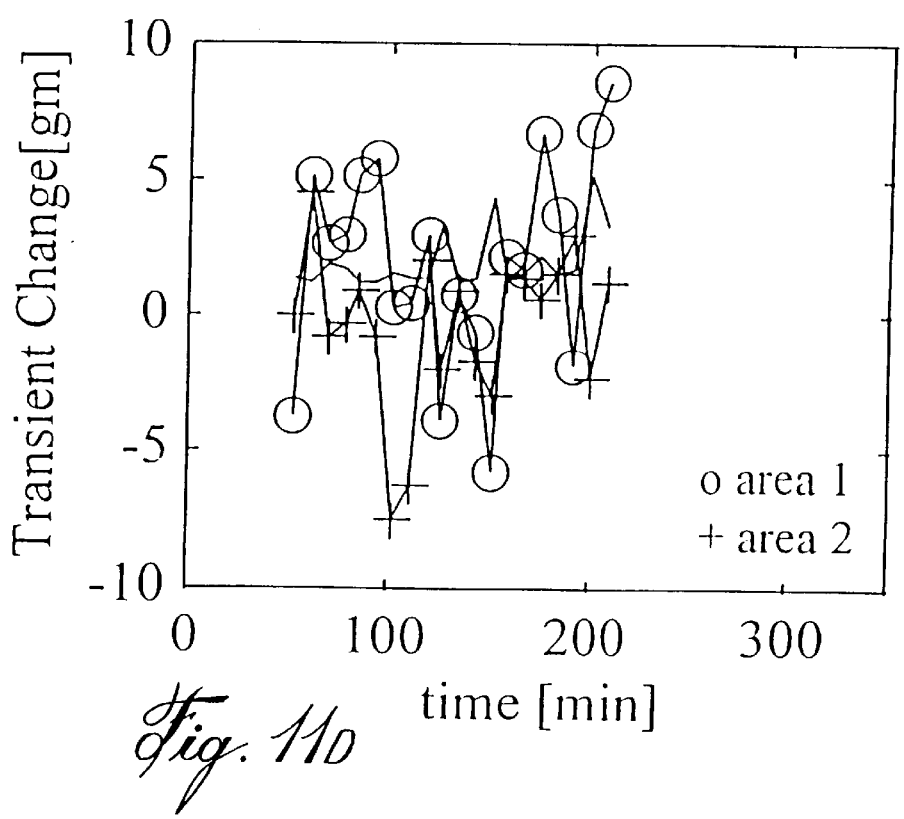
Figure 12:
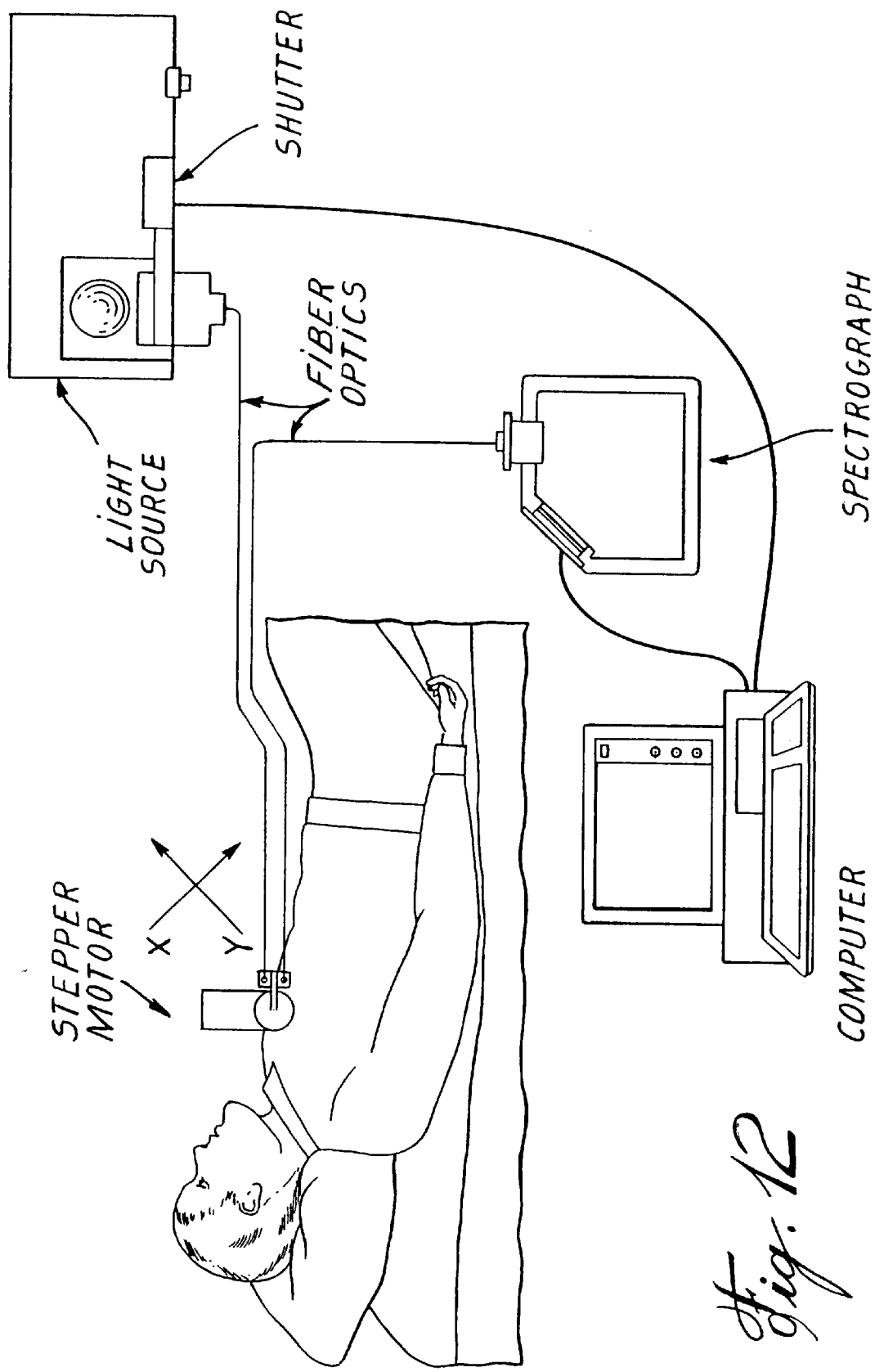
FIG. 12 illustrates an assembly similar to FIG. 1 for in vivo use.

FIG. 9) Estimates of Edema.

a) An absolute measure of edema b) Change in edema.

The calibration coefficients were used to estimate the increased water weight from a set of data not used in the construction of the calibration seen in FIG. (9A). The calibration attempted to correlate the true absolute weight increase with the estimate. As was seen with the phantom study, there is an offset between the true and estimated values. The slope and intercept of the estimation are 1.264 and −20.28 with a correlation coefficient of 0.972 and standard error of 2.585 gm. The weights response from the force transducer was a measure of the increase in weight with edema and not of the actual water present in the lung. An absolute measure is not possible, therefore, a change in the weight with respect to edema was estimated and shown in FIG. (9b). The estimated weight changes have a slope and intercept of 1.35 and −2.952 with a correlation coefficient of 0.976 and standard error of 2.757 gm.

The increase in hydrostatic pressure to produce edema also increases the blood volume to the lobe. To distinguish between a blood volume increase and edema, a transient response, similar to pulsed oximetry was used[17]. The transient was induced by momentarily increasing the hydrostatic pressure. Reflectance spectra were acquired before and after the increase. The fluid accumulation in the tissue produced a damped weight response associated with congestion. The normalized spectras seen in FIG. (6) were processed using a PLS regression.

The Weight Set from the PLS regression, consisted of linear combinations of the pure components in the spectra such as OH, CH, scattering, etc seen in FIG. (10). The first demonstrated approximately a linear relationship with wavelength consistent with scattering. The second again incorporated the scattering with an added water absorbance seen between 950–970 nm. The third consisted of a combination of the OH and CH contributions with the OH component dominating. The CH element in the spectra seen between 850–870 nm was small compared to the OH therefore the transient reduced the blood volume contribution in the spectra. The calibration coefficients were constructed from a set consisting of two dog experiments each with two locations. The coefficients were used to estimate the given set seen in FIGS. (11A,B). The transient weight changes decreased with time as a result of the accumulation of fluid. This change in the compliance of the lung was attributed to congestion. The weight change decrease ranged from 0.65% to 1.60% relative to the weight of the lobe. The calibration was used to estimate the change on two independent sets, FIGS. (11C,D). The NIR method ranged from 2.16% to 3.77%. In some cases, the estimates were skewed from the measured values towards the end of the run. The deviations were attributed to alveolar edema estimates made with a calibration constructed from interstitial edema. To verify the presence of interstitial and alveolar edema, the lobes were frozen for morphometry.

Each of the runs consisted of a control and two locations on the edematous lobe. Interstitial edema was seen in varying degrees in all the lobes, except for the controls. Different amounts of interstitial edema were observed for different locations on the same lobe which clearly demonstrated the inhomogenous nature of edema. The lobes with largest amounts of interstitial edema also exhibited alveolar flooding. The calibration constructed from the NIR spectras to estimate edema were based on lobes primarily with interstitial edema. The calibrations were unable to estimate alveolar edema using this calibration. The first case FIG. (11A), with no alveolar flooding performs very well in the NIR compared with the last FIG. (11D) with the largest amount. The NIR was an excellent method as a means of monitor interstitial edema.

The result has demonstrated that the change in water can be measured. The change in water has been estimated and a calibration performed with reasonable accuracy for the phantom and excised lungs. Simplifications were made in the use of a sponge as a model to mimic the response. The experiment assumed that the fluid accumulation in the sponge and in the lung were similar, which is not necessarily true. The fluid accumulation in the sponge is governed by the lattice structure. The spaces located in the sponge are much larger compared to an alveoli. The mean size of an alveoli is of the order of 100 $\mu$m compared to 400 $\mu$m in the sponge. Therefore, the amount of water trapped in the sponge at any given time is larger.

Thus a non-invasive spectroscopic method is presented for the measurement of pulmonary edema that involves acquiring diffuse reflectance spectra in the near-infrared region with change in water concentration, the latter being the main constituent of edema fluid. Both tissue phantom and excised lung were used to simulate edema. A partial least squares regression (PLSR) was used for the multivariate calibration in which the optimal number of factors was chosen based on the prediction error sum of squares (PRESS) of the calibration. A correlation coefficient of 0.9945 and standard error of 1.76 was obtained with the phantom. Edema formation in an in vitro lung was induced by elevating the hydrostatic pressure and measuring the edema as an increase in the total weight of the lung. The PLSR provided a correlation coefficient of 0.9779 and standard error of 2.16 for estimates of edema. The fluid accumulation changed the OH, CH, and scattering components in the NIR spectra. The scattering component, depicted as the baseline of the spectra, showed a steady change corresponding to interstitial edema. Alveolar flooding was represented as a sudden change in the spectral baseline. Histology of the lung was used to verify the presence of total edema, and to separate interstitial and alveolar edema components. To distinguish between a change in blood volume and edema, transient elevations in pulmonary venous pressure were produced. Thus NIR spectroscopy may be an alternative to radiological assessment of pulmonary edema.

5) In Situ Estimates Of Pulmonary Edema

In some studies, in-vitro dog lobes were used where the lobes were removed from the animal and measurement made externally. The objective is to make non-invasive edema measurements on the chest surface using the NIR spectroscopy. Towards this goal, an in-situ surface measure of pulmonary edema was made.

Figure 13A:
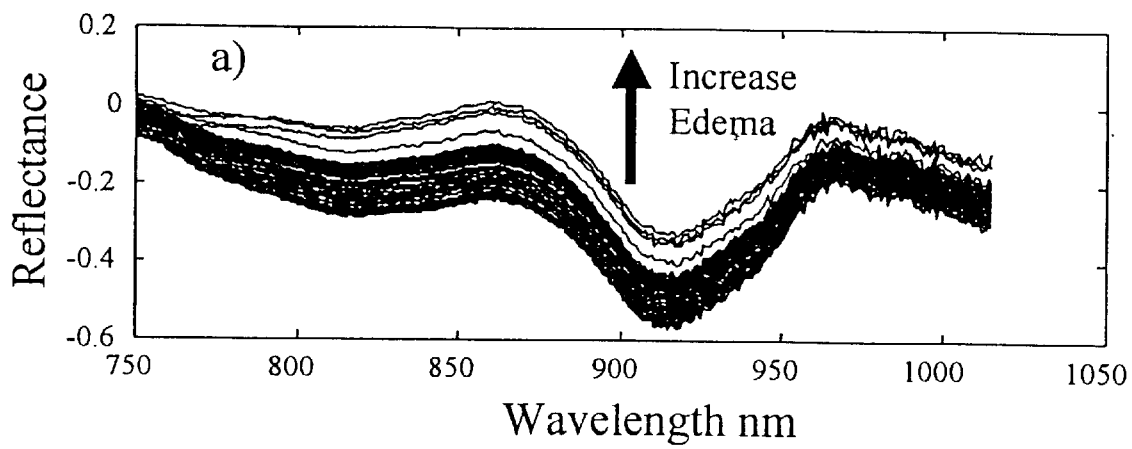
FIG. 13A shows a multiwavelength spectral response for in situ pulmonary edema.
Figure 13B:
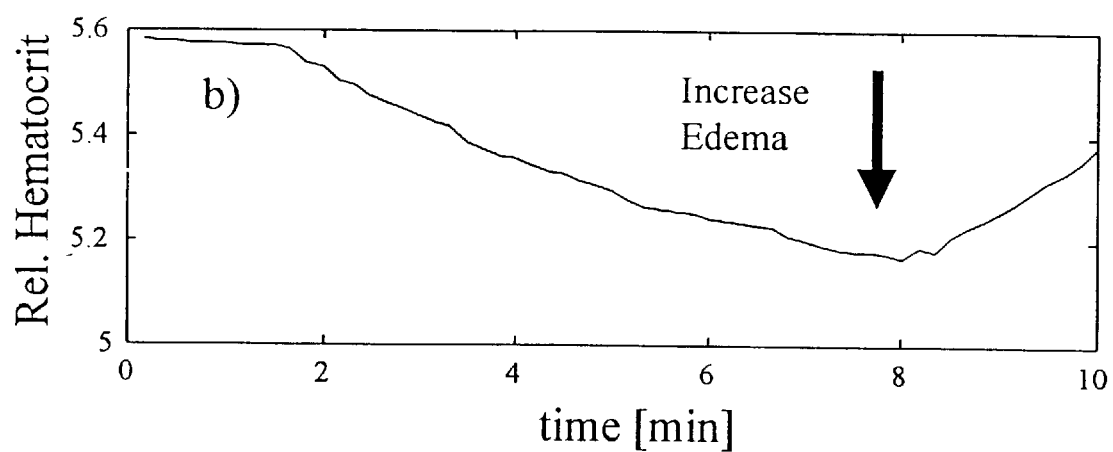
FIG. 13B shows relative hematocrit changes with time for in situ pulmonary edema.

The in-situ protocol was similar to the in-vitro study. Circulation to one of the lobes was isolated from the animal. The blood vessels (pulmonary artery and vein) were detached from the heart and connected to a blood reservoir. As with the in-vitro protocol, a reciprocating pump connected to the reservoir was used to pump blood to the lobe. The bronchial was connected to an external air supply maintained at 5-mmH$_2$O (49 pascals). Once the connections were made, the animal was sutured with the cannulas extruding out of the chest. Edema was induced with an increase in the vascular pressure through a change in the height of the blood reservoir. Since the lobe was isolated, it can be considered a closed system. Therefore, pulmonary edema can be monitored using an on-line relative hematocrit measurement, FIG. 13B.

Optical probes were placed on the surface of the chest approximately 4 cm from the sutured area. Diffuse reflectance measurements were made on surface of the chest simultaneously with the relative hematocrit, FIG. 13A. The spectra were collected at an integration time of 30 sec. At the conclusion of the experiment, the location was marked with india ink for histology. The spot on the lung was marked based on the location of the optical probes relative to the chest. The in-vivo lobe was also removed from the animal and used as a control for pulmonary edema. Both the control and the edematous lobes at the end of the experiment were cryogenically stored and transported to the Pathology Department at McGill University.

Figure 14:
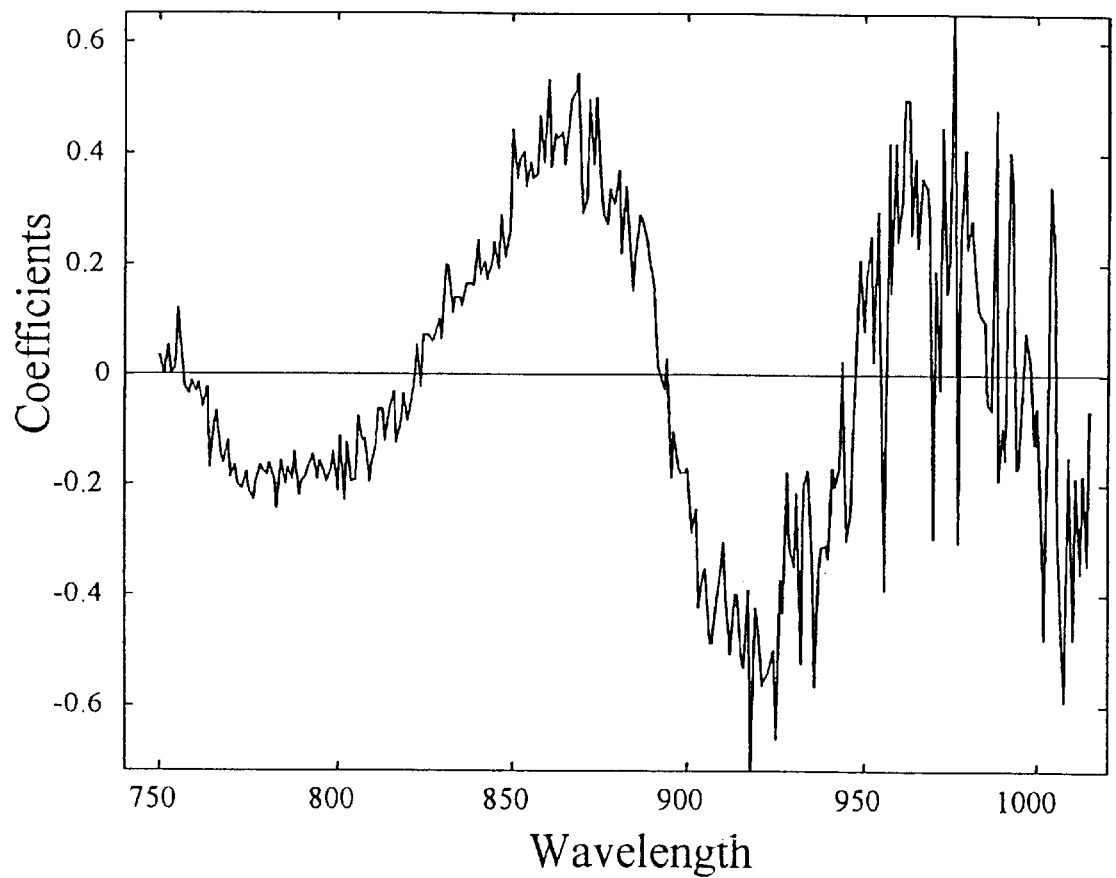
FIG. 14 is a plot of calibration coefficients with wavelength for in situ estimates of pulmonary edema.
Figure 15:
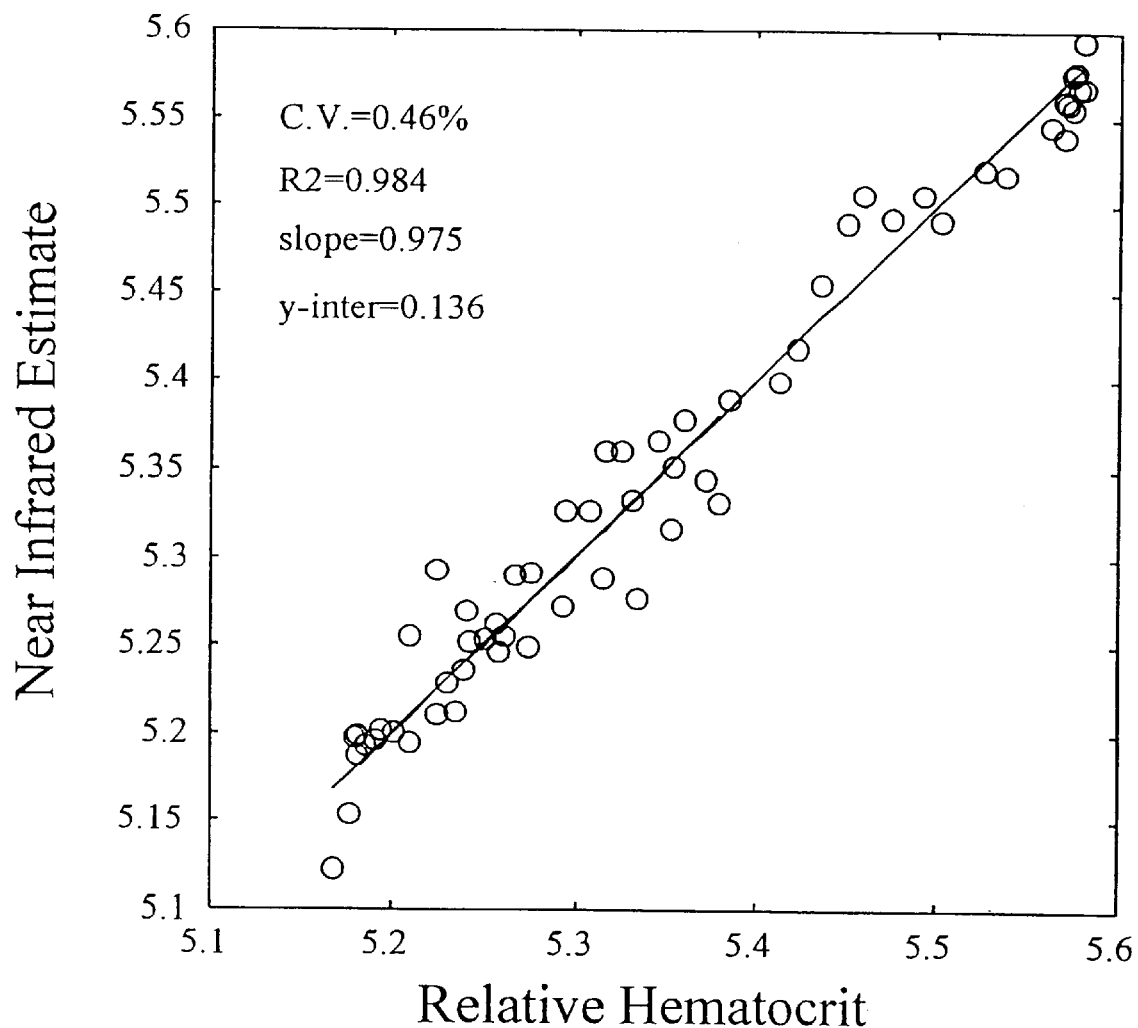
FIG. 15 is a plot of near infrared estimate against relative hematocrit for pulmonary edema.

The spectral data were processed using a multivariate calibration, namely, Partial Least Squares Regression (PLS). The calibration coefficients from the PLS regression consisting of wavelength dependent coefficients are demonstrated in FIG. 14. Applying these coefficients to the spectra produces the results in FIG. 15. The x-axes represent the values from the relative hematocrit estimate and the y-axes the estimates using the near infrared approach. The correlation of the hematocrit with the near infrared approach was 0.984 with a 4.6% error. The preliminary results indicate that a near infrared estimate through the chest wall is possible.

REFERENCES (1) Prichard, J. S. *Edema of the Lung*, Kugelmass N, Ed. Charles C Thomas; Springfield, Ill.,1982;pp165–226;

(2) Pistolesi, M and Giuntini, C *Assessment of Extravascular Lung Water, Radiologic Clinics of North America,* 1978, XVI (3), p551

(3) Harrison, M. O. Conte, P. J., and Heitzman, E. R. *Radiological Detection of clinically occult cardiac failure following myocardial infraction, British Journal Of Radiology,* 1971, 44, p578

(4) Stark, P. and Jasmine, J. *CT of Pulmonary Edema, Critical Reviews in Diagnostic Imaging,* 1989, Vol 29, pp. 245–255

(5) Mayo, J. R., Müller, N. L., Forster, B. B., Okazawa, M., and Paré, P. P., *Magnetic Resonance Imaging of hydrostatic pulmonary edema in isolated dog lungs: comparison with computed tomography, Journal of the Canadian Association of Radiologists,* 1990, Vol 41, pp281–286

(6) Wegenius, G. *Model Simulations of Pulmonary Edema Phantom Studies with Computed Tomography, Investigative Radiology,* 1991, Vol.26, pp. 149–156

(7) Cope, M., van der Zee, P., Essenpries M., Arridge, S. R., and Delpy D. T. *Data analysis methods for the near infrared spectroscopy of tissue: problems in determining the relative cytochrome aa$_3$ concentration, SPIE Vol.* 1431 *Time Resolved Spectroscopy and Imaging of Tissue,* 1991 pp251–262

(8) Arakaki, L. S. L. and Burns, D. H., *Multispectral Analysis for Quantitative Measurements of Myoglobin Oxygen Fractional Saturation in the Presence of Hemoglobin Interference, Applied Spectroscopy,* 1992, Vol.46 pp.1919–1928

(9) Mancini D. M., Bolinger L., Li H, Chance B., Wilson JR., *Validation of Near-Infrared Spectroscopy in Humans, Journal of Applied Physiology,* 1994 77(6): 2740–2747

10) Haida M. and Chance B., *A method to estimate the ratio of absorption coefficients of two wavelengths using phase modulated near infrared light spectroscopy, Advances in Experimental Medicine and Biology,* 1994 345:829–835

11) Luebbers D. W. *Chemical in vivo monitoring by optical sensors in medicine, Sensors and Actuators B-Chemical,* 1993 n1–3 pp. 253–262

12) Buijs K. and Choppin G. R., *Near-Infrared studies of the structure of water. I. Pure Water, Journal of chemical Physics,* 1963, 36(9)

13) Martens H. and Naes T. *Multivariate Calibration,* John Wiley and Sons, London; 1989, pp. 116–165

14) Haaland D. M. and Thomas E. V., *Partial Least Squares Methods for Spectral Analyses 1. Relation to other quantitative calibration methods and the extraction of qualitative information, Analytical Chemistry,* Vol.60 No.11, 1988 pp. 1193–1202;

15) Strang G., *Linear Algebra and Its Applications,* Academic Press, New York, 1976 pp. 130–138

16) Phelan M. K., Barlow, C. H., Kelly J. J., Jinguji T. M. and Callis J. B. *Measurement of caustic and caustic brine solutions by spectroscodic detection of the hydroxide ion in the Near-Infrared region 700–1150 nm, Analytical Chemistry,* 1989, 61, pp. 1419–1424

17) Marble D. R., D. H. Burns D. H., Cheung P. W. Diffusion-based model of pulse oximetry: in vitro and in vivo comparisons, Applied Optics, 1994, 33, pp. 1279–1285

TABLE 1

Pathology Results of Edema Lobes

| Expt. # | Lobe | Initial Weight [gm] | Final Weight [gm] | Weight Gain [gm] | Wet/ Dry Ratio | Interstitial Edema Grade | Alveoli Edema Percent |
|---|---|---|---|---|---|---|---|
| A | Control | | 44 | | 4.84 | 0.00 | 0 |
| A | Area 1 | 72 | 91 | 19 | 5.58 | 0.75 | 0 |
| A | Area 2 | | | | 5.34 | 0.25 | 0 |
| B | Control | | 45 | | 4.66 | 0.00 | 0 |
| B | Area 1 | 81 | 108 | 27 | 6.35 | 2.25 | 10 |
| B | Area 2 | | | | 6.16 | 2.00 | 5 |
| C | Con- | | 28 | | 4.85 | 0.00 | 0 |

TABLE 1-continued

Pathology Results of Edema Lobes

| Expt. # | Lobe | Initial Weight [gm] | Final Weight [gm] | Weight Gain [gm] | Wet/ Dry Ratio | Interstitial Edema Grade | Alveoli Edema Percent |
|---|---|---|---|---|---|---|---|
| | trol | | | | | | |
| C | Area 1 | 87 | 110 | 23 | 6.55 | 2.00 | 5 |
| C | Area 2 | | | | 6.01 | 2.00 | 0 |
| D | Control | | 39 | | 4.74 | 0.00 | 0 |
| D | Area 1 | 40 | 99 | 59 | 6.60 | 2.25 | 20 |
| D | Area 2 | | | | 7.42 | 2.25 | 15 |

What is claimed is:

1. A method of detecting pulmonary edema in a lung comprising:
   a) exposing a lung under investigation to infrared radiation,
   b) measuring reflected infrared radiation scattered by the lung as a spectral response to the presence of water in the lung,
   c) comparing the reflected radiation with calibrated values of reflected radiation for lung water levels indicative of pulmonary edema, and
   d) evaluating occurrence of pulmonary edema in the lung from the comparison developed in step c).

2. A method according to claim 1 wherein said infrared radiation in step a) is near infrared radiation having a wavelength between 700 and 2500 nm.

3. A method according to claim 2 wherein said wavelength is between 600 and 1300 nm.

4. A method according to claim 3 wherein said lung is exposed to said radiation in step a) at a plurality of sites of the lung, and step b) comprises measuring the reflected radiation scattered by said plurality of sites.

5. A method according to claim 2 wherein said lung is exposed to said radiation in step a) at a plurality of sites of the lung, and step b) comprises measuring the reflected radiation scattered by said plurality of sites.

6. A method according to claim 1 wherein said lung is exposed to said radiation in step a) at a plurality of sites of the lung, and step b) comprises measuring the reflected radiation scattered by said plurality of sites.

7. An apparatus comprising:
   i) a plurality of optical fibers effective to transmit infrared radiation from a source to a medium under investigation and to transmit reflected scattered radiation from said medium,
   ii) a source of infrared radiation operatively associated with said fibers for transmission of infrared radiation,
   iii) detector means for receiving reflected scattered radiation from said fibers and issuing signals responsive thereto, and
   iv) evaluating means for receiving said signals and comparing the received signals with calibrated values, characterized in that said apparatus is for detecting pulmonary edema, said fibers i) are effective to transmit said infrared radiation from said source to a lung under investigation and to transmit reflected scattered radiation from the lung, and said evaluating means iv) is adapted to compare the received signals with calibrated values for pulmonary edema.

8. Apparatus according to claim 7 wherein said source is adapted to transmit near infrared radiation having a wavelength between 700 to 2500 nm.

9. Apparatus according to claim 7 wherein said source is adapted to transmit near infrared radiation having a wavelength between 600 and 1300 nm.

10. Apparatus according to claim 7 wherein said optical fibers are adapted to transmit infrared radiation to a plurality of sites of the lung under investigation, and said detector means is adapted to measure the reflected scattered radiation from the plurality of sites.

11. Apparatus according to claim 7 wherein said evaluating means iv) is adapted to compare the received signals with calibrated values of reflected radiation for lung water indicative of pulmonary edema.

* * * * *